United States Patent [19]

Neugebauer et al.

[11] 4,087,462
[45] May 2, 1978

[54] PRODUCTION OF FORMALDEHYDE IN A FLUIDIZED BED WITH A FIXED TEMPERATURE GRADIENT

[75] Inventors: Walter Neugebauer, Schlangenbad-Georgenborn; Heinz Friedrich, Grossauheim, both of Germany

[73] Assignee: Deutsche Gold- und Silber-Scheideanstalt Vormals Roessler, Frankfurt, Germany

[21] Appl. No.: 438,462

[22] Filed: Jan. 31, 1974

[30] Foreign Application Priority Data

Feb. 1, 1973  Germany .............................. 2304762

[51] Int. Cl.² ............................................. C07C 45/16
[52] U.S. Cl. ................................................. 260/603 C
[58] Field of Search ................................. 260/603 HF

[56] References Cited

U.S. PATENT DOCUMENTS

| | | | |
|---|---|---|---|
| 2,649,420 | 8/1953 | MacLean | 260/603 HF |
| 2,735,743 | 2/1956 | Rex | 423/1 |
| 3,843,562 | 10/1974 | Friedrich et al. | 260/603 HF |

OTHER PUBLICATIONS

Averbukh et al., Chem. Abstracts, vol. 67, 53581e, 1967.
Amundson et al., Chem. Abstracts, vol. 60, 204, 1964.

*Primary Examiner*—James O. Thomas, Jr.
*Assistant Examiner*—G. T. Breitenstein
*Attorney, Agent, or Firm*—Cushman, Darby & Cushman

[57] ABSTRACT

Formaldehyde is prepared by gas phase reaction of methanol with oxygen in a fluidized bed of an oxide catalyst in which the arrangement of the particles in the fluidized bed provides a negative temperature gradient in the direction of gas flow.

6 Claims, No Drawings

PRODUCTION OF FORMALDEHYDE IN A FLUIDIZED BED WITH A FIXED TEMPERATURE GRADIENT

The present invention is directed to a process for the production of formaldehyde from methanol and air on an oxide catalyst in a fluidized bed.

Formaldehyde is made industrially from methanol and air on a silver catalyst and recently also on oxide catalysts. The oxide catalyst process is carried out on a large scale in tube bundle reactors. Because of the exothermy in the formaldehyde formation the diameter of the reaction tubes is limited in favor of a sufficient removal of heat; because of which, for efficient equipment, a large number of reaction tubes must be installed.

To avoid the above-named disadvantages of tube bundle reactors it has already been proposed to carry out the oxidation of methanol to formaldehyde in a fluidized bed (Meissner, German Auslege schrift No. 1,162,343). However, known disadvantages of the fluidized bed technique are the formation of bubbles which lead to the breakthrough of unreacted methanol constituent, as well as the back mixing of gas in the upper part of the fluidized bed which increases the residence time of formaldehyde and which has as a consequence the undesired further combustion to carbon monoxide. To eliminate both of these disadvantages, especially to eliminate the bubble formation there has been proposed recently the insertion of quieting installations in the fluidized bed, thus, for example, note T. Ishii and G. L. Osberg in regard to the "Isomerization of Cyclopropane" in *A. I. Ch. E. Journal, Vol.* 11 (1965), pages 279-285.

As especial advantage of a fluidized bed there has been observed in the literature the uniform temperature distribution inside the fluidized bed. However, it appears that this supposed advantage of the fluidized bed in the present reaction of methanol with air also promotes the formaldehyde yield reducing reaction $$HCHO + \tfrac{1}{2}O_2 \rightarrow CO + H_2O$$

which is not the case for example in solid bed in which there is generally built in a temperature gradient.

It has now been found that surprisingly high methanol reaction and very good formaldehyde yields are obtained if a definite negative temperature gradient is established through the fluidized bed in reference to the direction of flow of the reaction compounds through the influencing of the free particle movement by means of installations.

According to a preferred form of the process the temperature gradient is chosen between 0.1 and 2.0° C./cm., more suitably to about 1° C./cm. fluidized bed height.

As installations in the process of the invention there are suitably arranged inside the fluidized bed perpendicular to the direction of flow wire gauzes or lattices or perforated plates, wire spirals or layers of deflecting bodies such as rings or Berl saddles, tube cuttings or cylinders and the like.

The installation of a definite temperature gradient not only effects the attainment of a nearly complete methanol reaction but also an improved yield of charge over the previously known processes and an increase of the catalyst service life.

On account of the installation of the temperature gradient according to the invention there is always the reaction of the main part of the methanol in a relatively short zone of higher temperature while the residual amounts react at lower temperatures in which also the decomposition reaction of the formaldehyde is substantially depressed with the result of improvement of yield.

A further advantage of the process of the invention is that a change of the speed of flow at otherwise equal parameter makes possible an influence of the temperature gradient in narrow ranges; a reduction of the speed of flow effects an increase of the temperature gradient; an increase of the speed of flow, a reduction in the temperature gradient.

Any of the solid oxide catalysts used in the formation of formaldehyde from methanol and oxygen in the gaseous phase can be employed in particulate form as the fluidized bed in the present invention and the catalyst per se is not part of the invention. Thus, there can be used iron-molybdenum oxides, e.g., $MoO_3$–$Fe_2O_3$ weight ratio about 4 : 1, iron-molybdenum-titanium oxides, *) iron-molybdenum oxides on Kieselguhr.

*) iron-molybdenum-cobalt oxides, bismuthphosphorus-molybdenum-silicium oxides on kieselguhr, The process of the invention will be further explained in the following examples.

The experiments on which the examples are based were carried out in a reactor having a diameter of 200 mm which was loaded with a catalyst of iron-molybdenum-titanium oxides ($Fe_2O_3$ . $MoO_3$ . $TiO_2$, weight ratio 1 :4 : 2.1).

EXAMPLES 1 TO 5

The catalyst was added in a particle size between 0.3 to 2 mm and in an amount of 8 kg. The gases added (methanol plus air) amounted to 14 normal m³/kg catalyst . hour and had a methanol concentration of 13.7 volume %.

The gas inlet temperature was 180° C., the maximum temperature of the fluidized bed was 420° C. In Table 1 there are collected the different negative temperature gradients in the fluidized bed caused by various installations and the experiments show the values for conversion, yield, catalyst productivity and carbon monoxide formation based on the size of the negative temperature gradient.

EXAMPLES 6 AND 7

There were always used 15 kg of catalyst having a particle size of 0.3 to 1.5 mm. The gas inlet temperature was 150° C. and the temperature of the fluidized bed was 400° C. These temperatures thus were somewhat lower than in examples 1 to 5. The gas added (methanol plus air) amounted to 7 normal m³/kg catalyst . hour, and contained 18.8 volume % of methanol. In example 6 the fluidized bed was operated without installations with a temperature gradient of 0, in example 7 with 50 gauzes having a mesh width of 5 mm and always at intervals of 3 cm. The negative temperature gradient in example 7 was 0.6° C./cm.

EXAMPLE 8

The amount of catalyst was 10 kg and it had a particle size of 0.3 to 2 mm, the gas added was 10 normal m³/kg catalyst . hour and contained 14.2 volume % methanol (balance of the gas was air). The entrance temperature was 130° C., temperature of the fluidized bed 405° C. and the negative temperature gradient 1.0° C./cm.

which was effected by insertion of 25 liter of so called PALL rings *) in the reaction space.

*) see German Patent 853159

The results of experiments 6 to 8 are contained in Table 2.

Table 1

| Example No. | Temp. Gradient °C/cm | Installations | Methanol Conversion Mole % | Formaldehyde Yield Based On | | Catalyst Productivity kg CH$_2$O/kg. hr. | Carbon monoxide mole % |
|---|---|---|---|---|---|---|---|
| | | | | Conversion Mole % | Starting Material Mole % | | |
| 1 | 0.0 | None | 92.6 | 90.1 | 83.4 | 2.14 | 9.2 |
| 2 | 0.2 | 10 gauzes all at 10 cm intervals | 96.5 | 93.5 | 90.3 | 2.32 | 6.2 |
| 3 | 1.0 | 5 gauzes at intervals of 6 cm; 20 gauzes at intervals of 3 cm. | 98.8 | 94.8 | 93.7 | 2.40 | 5.0 |
| 4 | 1.15 | 31 gauzes at intervals of 3 cm | 99.1 | 95.0 | 94.1 | 2.42 | 5.0 |
| 5 | 1.8 | 50 gauzes at intervals of 2 cm | 99.5 | 93.5 | 93.0 | 2.38 | 6.5 |

Table 2

| Example No. | Temp. gradient °C/cm | Installations | Methanol Conversion Mole % | Formaldehyde Yield Based On | | Catalyst productivity kg CH$_2$O/kg . hr | Carbon Monoxide Mole % |
|---|---|---|---|---|---|---|---|
| | | | | Conversion Mole % | Starting Material Mole % | | |
| 6 | 0.0 | None | 95.6 | 91.2 | 87.2 | 1.54 | 8.4 |
| 7 | 0.6 | 50 gauzes at intervals of 3 cm | 99.1 | 95.4 | 94.5 | 1.67 | 4.6 |
| 8 | 1.0 | 25 liter PALL rings | 99.3 | 95.3 | 94.6 | 1.80 | 4.7 |

The results of Tables 1 and 2 show in comparison to examples 1 and 6 on the one hand and 2 to 5, 7 and 8 on the other hand that the production of a temperature gradient in the fluidized bed exerted a positive influence on all parameters which are determinative for the industrial and economical success of the process and therewith led to a considerable improvement in the process.

What is claimed is:

1. In a process for the production of formaldehyde by the gas phase reaction of methanol with oxygen in a fluidized bed of a solid oxide catalyst the improvement comprising carrying out said reaction with a negative temperature gradient through the fluidized bed of from 0.1° to 2.0° C./cm. of fluidized bed height in the bed in the direction of gas flow.

2. A process according to claim 1 wherein there are provided in the fluidized bed installations arranged to provide said temperature gradient.

3. A process according to claim 1 wherein the temperature gradient is about 1.0° C./cm. of fluidized bed height.

4. A process according to claim 1 wherein the fluidized bed is formed of a catalyst of iron-molybdenum-titanium oxides.

5. A process according to claim 2 wherein the installations are pall rings.

6. A process according to claim 2 wherein the installations are gauzes.

* * * * *